US007359537B2

(12) United States Patent
Mori (10) Patent No.: US 7,359,537 B2
(45) Date of Patent: Apr. 15, 2008

(54) DNA MICROARRAY IMAGE ANALYSIS SYSTEM

(75) Inventor: Atsushi Mori, Tokyo (JP)

(73) Assignee: Hitachi Software Engineering Co., Ltd., Tokyo (JP)

( * ) Notice: Subject to any disclaimer, the term of this patent is extended or adjusted under 35 U.S.C. 154(b) by 721 days.

(21) Appl. No.: 10/853,178

(22) Filed: May 26, 2004

(65) Prior Publication Data

US 2004/0240718 A1 Dec. 2, 2004

(30) Foreign Application Priority Data

Jun. 2, 2003 (JP) ............................. 2003-156206

(51) Int. Cl.
*G06K 9/00* (2006.01)
(52) U.S. Cl. ...................... 382/129; 382/156; 382/157; 382/159
(58) Field of Classification Search ................ 382/157, 382/160, 129, 156, 159
See application file for complete search history.

(56) References Cited

U.S. PATENT DOCUMENTS

2003/0142094 A1* 7/2003 Zhang ........................ 345/440

FOREIGN PATENT DOCUMENTS

JP 7-306149 7/1993
JP 2002-189026 8/2001

OTHER PUBLICATIONS

Schmidt, W. et al., "Pattern Recognition Properties of Various Feature Spaces for Higher Order Neutral Networks", IEEE Transactions on Pattern Analysis Machin Intelligence, Aug. 1993, pp. 795-801.*
Hautaniemi Sampsa et al: "A novel strategy for microarray quality control using Bayesian networks." Bioinformatics (Oxford, England) Nov. 1, 2003, vol. 19, No. 16, Nov. 1, 2003, pp. 2031-2038, XP002403872 ISSN: 1367-4803.*

(Continued)

*Primary Examiner*—Bhavesh M. Mehta
*Assistant Examiner*—John B Strege
(74) *Attorney, Agent, or Firm*—Reed Smith LLP; Stanley P. Fisher, Esq.; Juan Carlos A. Marquez, Esq.

(57) ABSTRACT

In a microarray image analysis system, when one of a plurality of statuses is set for a spot of a microarray by the user, the status of a similar spot is automatically determined. In a microarray image, the user determines a status of a spot, the pixel value matrix of an image in a spot region is learned by a neural network, a vertically and horizontally symmetrical image and an image rotated about the center of the region are formed and are learned by the neural network, and the neural network formed by repeating these steps is used for automatically recognizing the status of an undecided spot.

7 Claims, 7 Drawing Sheets

OTHER PUBLICATIONS

Bicego, M. et al. "A supervised data-driven approach for microarray spot quality classification", Springer-Verlag London Limited, Jun. 11, 2005, pp. 181-187.

Schmidt, W. et al., "Pattern Recognition Properties of Various Feature Spaces for Higher Order Neutral Networks", IEEE Transactions on Pattern Analysis Machin Intelligence, Aug. 1993, pp. 795-801.

Hautaniemi, S. et al., "A novel strategy for microarray quality control using Bayesian networks", Bioinformatics, 2003, vol. 19 No. 16, pp. 2031-2038.

Ruosarri, S. et al. "Image Analysis for Detecting Faulty Spots from Microarray Images", Springer-Verlag Berlin Heidelberg, 2002, pp. 259-266.

Buhler, J. et al. "Dapple: Improved Techniques for Finding Spots on DNA Microarrays", UW CSE Technical Report UWTR, Aug. 5, 2000, pp. 1-12.

* cited by examiner

DNA MICROARRAY IMAGE ANALYSIS SYSTEM

BACKGROUND OF THE INVENTION

1. Field of the Invention

The present invention relates to a pattern recognition system for handling an image of a DNA microarray and particularly relates to an image analysis system for a Stanford type microarray having a plurality of blocked spots.

2. Background Art

Stanford type microarrays are available which have a plurality of blocked spots. For example, one microarray has 4×8 blocks each of which is constituted of X×Y spots. After a specimen is brought into contact with the microarray, a fluorescent intensity of each spot is optically measured. In the optical measurements, each spot is divided into N×M pixels and the pixels are sequentially or simultaneously measured. Since a quite a number of measurements are performed with a massive amount of data, microarray image analysis systems are developed to perform statistical analysis on obtained data.

For example, as to automatic recognition of the position and size of a spot in a microarray, a filtering system described in JP Patent Publication (Kokai) No. 2002-189026 is known. The system described in the document performs processing such as filtering, segmentation, and morphological operation during an automatic analysis on an image of a microarray and the like so that useful information is separated from various noise sources causing an erroneous interpretation.

As described in the document, the system automatically recognizing the position and size of a spot after filtering is available. However, a flag is manually set by changing the status of a spot lacking reproducibility and quantitativeness. The flag is set to remove the spot in the subsequent data analysis.

An example of a spot lacking reproducibility and quantitativeness includes a spot with dirt, a damaged spot, and a doughnut-shaped spot. A similar status needs to be set for a spot symmetrical with respect to the center of a spot region.

Further, according to the characteristic of a method of producing a microarray, spots having similar spot coordinates in a block are prone to have similar statuses.

An object of the present invention is to provide a system for semi-automatically setting a flag on a spot. The flag is manually set by the user at present.

SUMMARY OF THE INVENTION

In order to attain the above object, the present invention relates to a DNA microarray image analysis system comprising status automatic setting means for setting spot regions in a DNA microarray image after hybridization and then automatically setting one of a plurality of statuses which can be arbitrarily set by the user for each of the spot regions, learning means for learning the set status by using a pixel value of each of the spot regions and storing the learning results in storage means, and automatic decision means for performing automatic decision using the learning results.

The status of the present invention indicates a state of each spot that is significant in a microarray analysis and is also referred to as a flag. The kind of status includes the presence (abnormal) or absence (normal) of a problem in an analysis, the presence or absence of a spot, the presence or absence of dirt, and an abnormal shape of a spot. Other kinds of status may be properly set in response to the needs of an analyzer.

Further, in the present invention, an automatically set status is learned using a pixel value of each of the spot regions and the number of stored learning results is not particularly limited. An analyzer can set the number of stored learning results as appropriate in consideration of the kind of status, a demanded analysis accuracy, and the number of test samples.

In the present invention, it is preferable that the means for automatically setting one status is constituted of a feed-forward neural network where a status set by the user is a teacher signal (training data).

Besides, it is preferable that input serving as a teacher signal (training data) to the feed-forward neural networks is each pixel value included in a spot region selected by the user.

Moreover, input serving as a teacher signal (training data) to the feed-forward neural network may be each pixel value included in a selected image which is horizontally, vertically, or vertically and horizontally reversed, instead of each pixel value included in the selected spot region. Similarly instead of a pixel value included in an image, input serving as a teacher signal (training data) to the feed-forward neural network may be each pixel value included in an image rotated by 90°, 180°, or 270°. According to the graphical symmetry of spots to be set at the same status, the vertically and horizontally reversed image and the rotated image are also used as teacher signals, thereby enriching the teacher signal (training data) with little learning.

It is preferable that input serving as a teacher signal (training data) to the feed-forward neural network is each pixel value included in an image and a value indicating a spot position in a block.

Moreover, each pixel value included in a spot region with an undecided status may be inputted to the feed-forward neural network after learning, expected values may be calculated for a plurality of statuses, and a status with the highest expected value may be outputted out of the expected values of the plurality of statuses.

Additionally, the microarray of Stanford type with a plurality of blocked spots is preferable for implementing the microarray analysis system of the present invention.

Furthermore, the user can optionally select the function of automatically setting similar statuses for spots having similar spot coordinates in a block.

The feed-forward neural network configured thus is made storable and readable so as to increase the ability of the feed-forward neural network. The present invention enables the user to select a feed-forward neural network according to the manufacturing state of a chip.

DETAILED DESCRIPTION OF THE PREFERRED EMBODIMENTS

An embodiment of the present invention will be specifically described below in accordance with the accompanying drawings.

Figure 1:
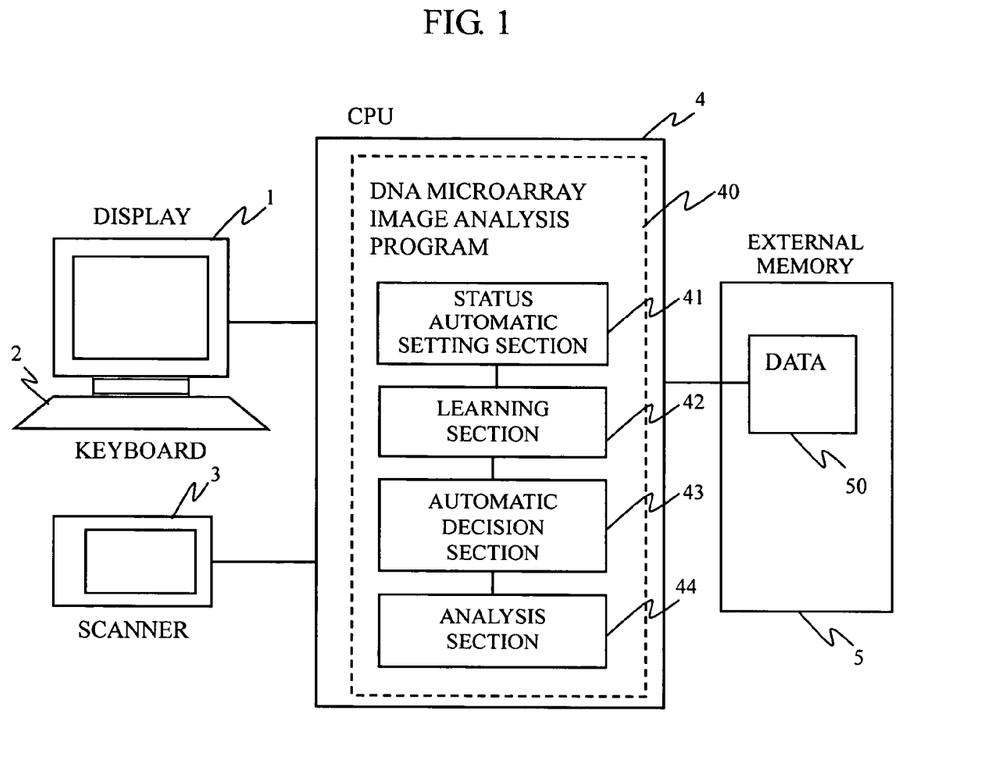
FIG. 1 is a hardware structural diagram showing a microarray image analysis system according to the present invention.

FIG. 1 is a diagram showing an example of the configuration of a DNA microarray image analysis system according to the present invention. The system is broadly constituted of input/output devices including a display 1, a keyboard 2, and a scanner 3, a CPU 4, and an external memory 5. A DNA microarray image analysis program 40 is stored in the memory region of the CPU 4. The DNA microarray image analysis program 40 is composed of a status automatic setting section 41 for automatically setting one of a plurality of statuses which can be arbitrarily set by the user for each spot region of a DNA microarray image after hybridization, a status learning section 42 for learning the set status by using a pixel value of each spot region and storing the learning results in the external memory 5, an automatic decision section 43 for performing automatic decision by using the learning results, and an analysis section 44 using the above-described means. The external memory 5 stores data 50 which includes data read by the scanner 3 and the learning results. The DNA microarray image analysis program 40 can be provided through recording media such as a floppy (trademark) disk, a CD-ROM, a DVD-ROM, and an MO. Alternatively the DNA microarray image analysis program 40 can be provided through a communication network such as the Internet.

Figure 2:
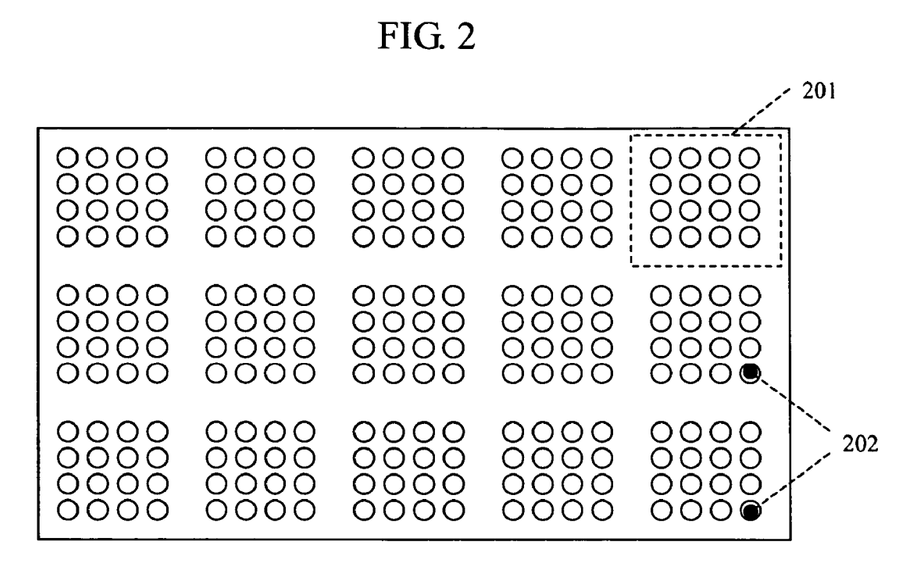
FIG. 2 is a diagram showing an image of a DNA microarray.

FIG. 2 is a diagram showing an image of a DNA microarray. FIG. 2 shows a kind of microarray which is spotted in blocks according to the structure of a spotter. Reference numeral 201 denotes the range of one block. Reference numeral 202 denotes examples of spots having similar spot coordinates in blocks.

Figure 3:
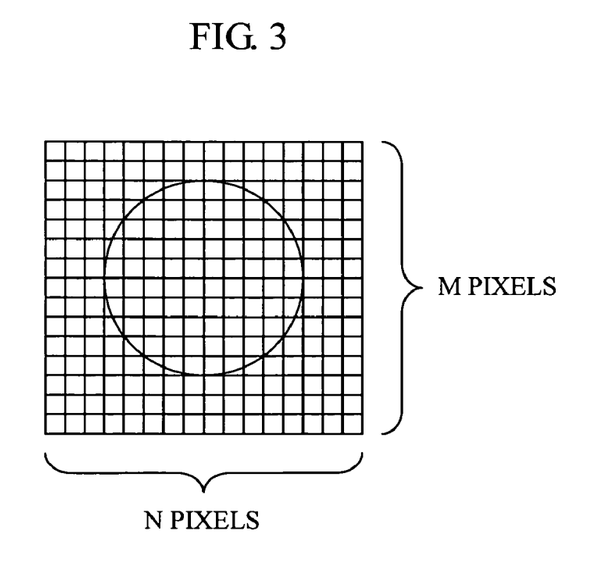
FIG. 3 is an enlarged view showing a spot.

FIG. 3 is an enlarged view of a spot region. The fluorescence intensities of N×M pixels are converted into numbers.

Figure 4:
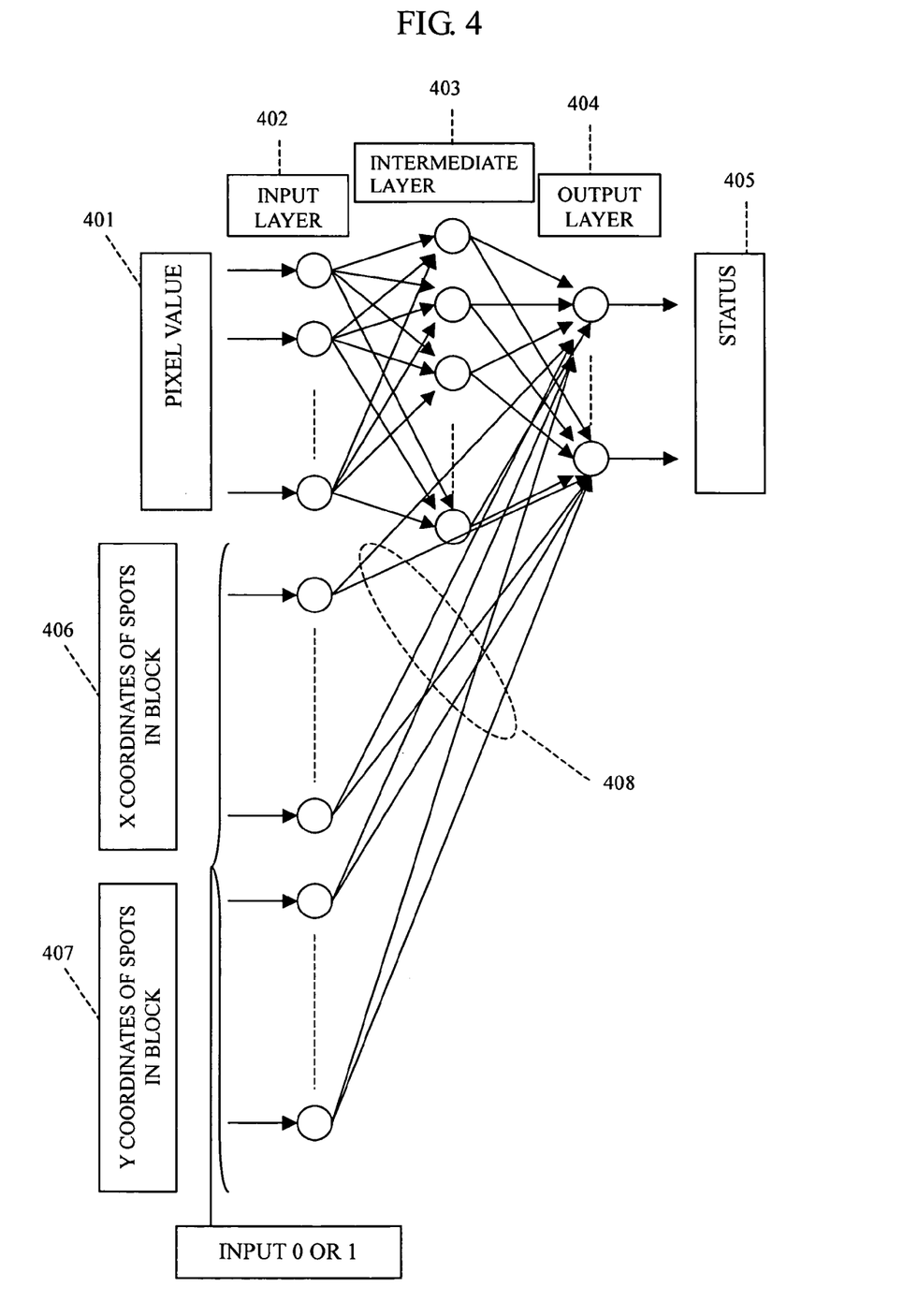
FIG. 4 is a conceptual diagram showing a feed-forward neural network.

FIG. 4 is a conceptual diagram showing a feed-forward neural network. Reference numeral 401 indicates that the fluorescence intensities of the M×N pixels that are converted into numbers are inputted to an input layer according to FIG. 2. Reference numeral 402 denotes the input layer of the feed-forward neural network. The number of input units for pixel values is equal to the number of pixels in the spot region and the number of units for inputting spot positions in a block is equal to the number of X-coordinate spots+the number of Y-coordinate units. An output function is a linear function. Reference numeral 403 denotes an intermediate layer of the feed-forward neural network. An output function is a logistic function shown in FIG. 5. Reference numeral 404 denotes an output layer of the feed-forward neural network. The number of units is equal to the number of kinds of statuses to be set. An output function is the logistic function shown in FIG. 5. Reference numeral 405 denotes a status determined by the output values of the output layer. When a sigmoid function is used as the logistic function, a value close to 1 or 0 is outputted. A value close to 1 is regarded as a status corresponding to an output unit. In the case of a system not permitting the setting of two or more statuses for one spot, a status of an output unit closest to 1 is adopted.

Reference numeral 406 indicates that the X coordinates of spots in a block of FIG. 2 are inputted. 1 is inputted only to units corresponding to the X coordinates and 0 is inputted to the other units. In the case of a setting not using spot coordinates in a block, 0 is inputted to all the units in 406 and thus the X coordinates of the spots in the block do not affect the output of a status. Reference numeral 407 indicates that the Y coordinates of spots in a block of FIG. 2 are inputted. 1 is inputted only to units corresponding to the Y coordinates and 0 is inputted to the other units. In the case of a setting not using spot coordinates in a block, 0 is inputted to all the units in 407 and thus the Y coordinates of the spots in the block does not affect the output of a status.

Reference numeral 408 indicates that the input of spot coordinates in the block is directly outputted to the output layer without passing though the intermediate layer. Hence, the decision of a status according to pixel values and the decision of a status according to spot coordinates in a block produce independent networks. The sum of results serves as the output of a status.

In 405, a status is decided by each output value.

Figure 5:
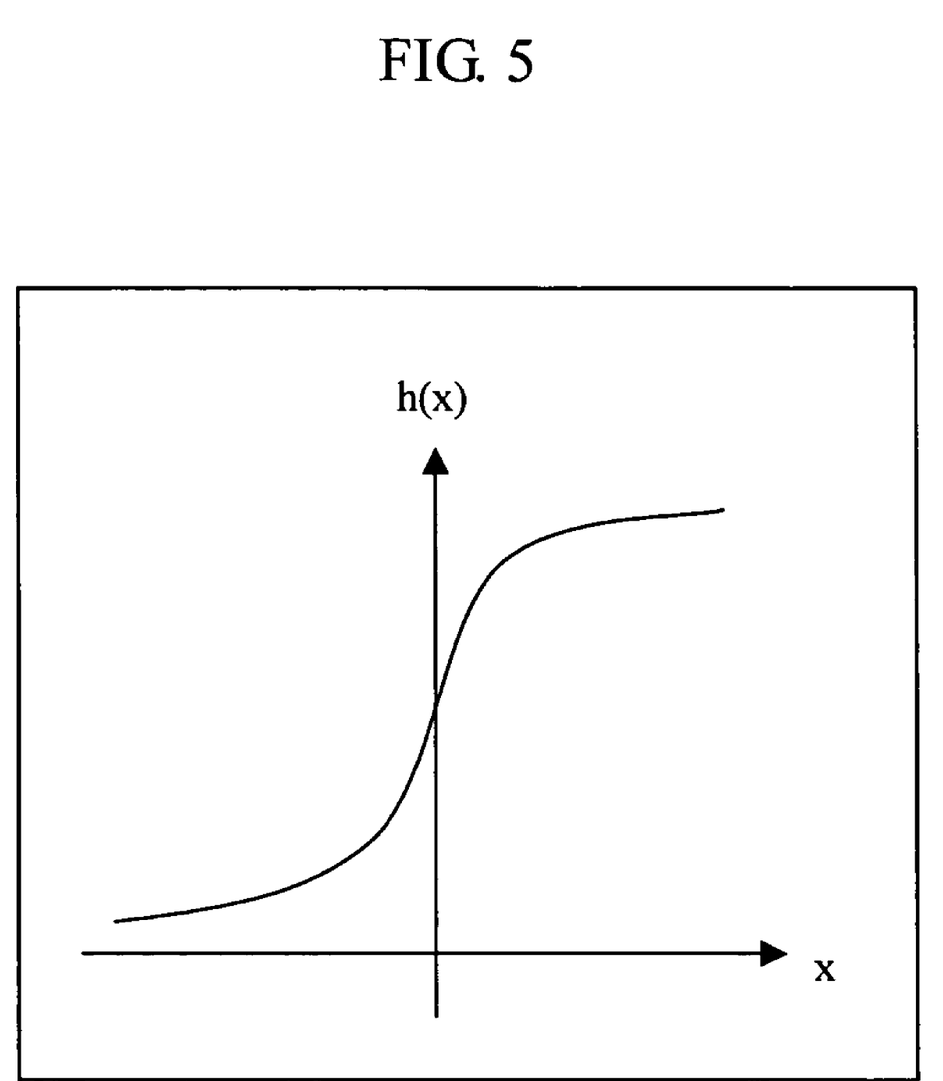
FIG. 5 is a diagram showing a logistic function.

FIG. 5 shows a logistic function which is frequently used for feedback error learning in a neural network and is a differentiable function similar to a step function. A function having the minimum value of 0 and the maximum value of 1 is called a sigmoid function, which is used for the output layer requiring the output of 0 or 1 in the present invention.

Figure 6:
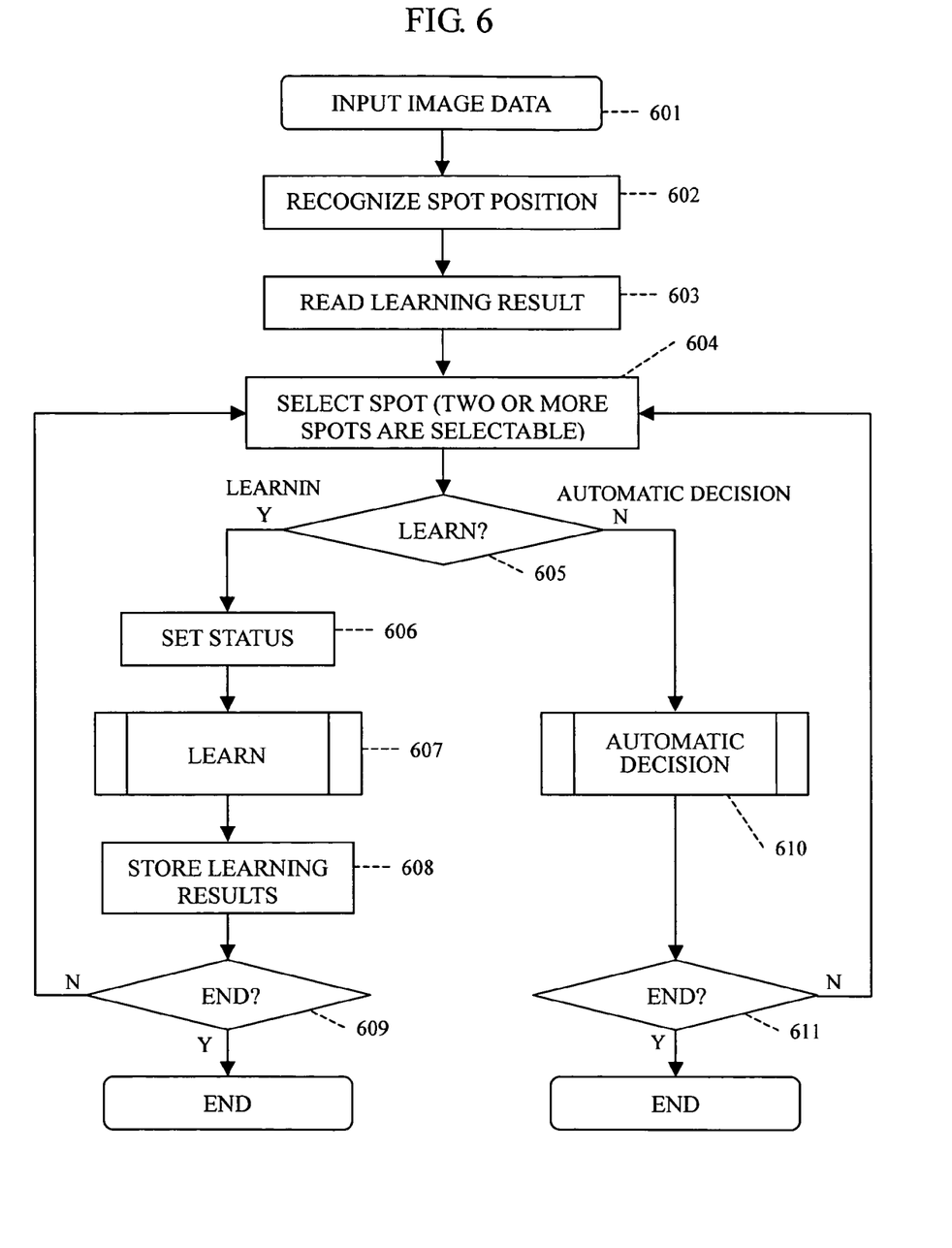
FIG. 6 is an overall flowchart showing the present invention.

FIG. 6 is a flowchart showing the overall flow of DNA microarray image analysis. A part for learning and a part for automatic decision will be described in the subsequent drawings. Step 601 is a starting step where image data obtained from experiment results using a DNA microarray is inputted to a system including the present invention. The image data includes a scanned fluorescent intensity. Step 602 is associated with the input of a pixel value according to the present invention and spot regions are decided in this step. Processing from step 603 relates to the present invention. When the learning results of the feed-forward neural network have been stored in this step, the learning results can be read in this step.

In step 604, the user selects a spot for learning or automatic decision. Two or more spots can be selected.

In step 605, the user selects learning or automatic decision.

When the user selects learning in step 605, the user sets a status, in step 606, for a spot selected in step 604. Step 607 is a learning step which is specifically shown in FIG. 7. In step 608, learning results are stored. When the user desires, learning results are stored in this step. In step 609, the user decides whether the system should be ended or not. When the system is not ended, for example, when another status is set or automatic decision is performed, the processing returns to step 604 and a spot is selected again.

Figure 8:
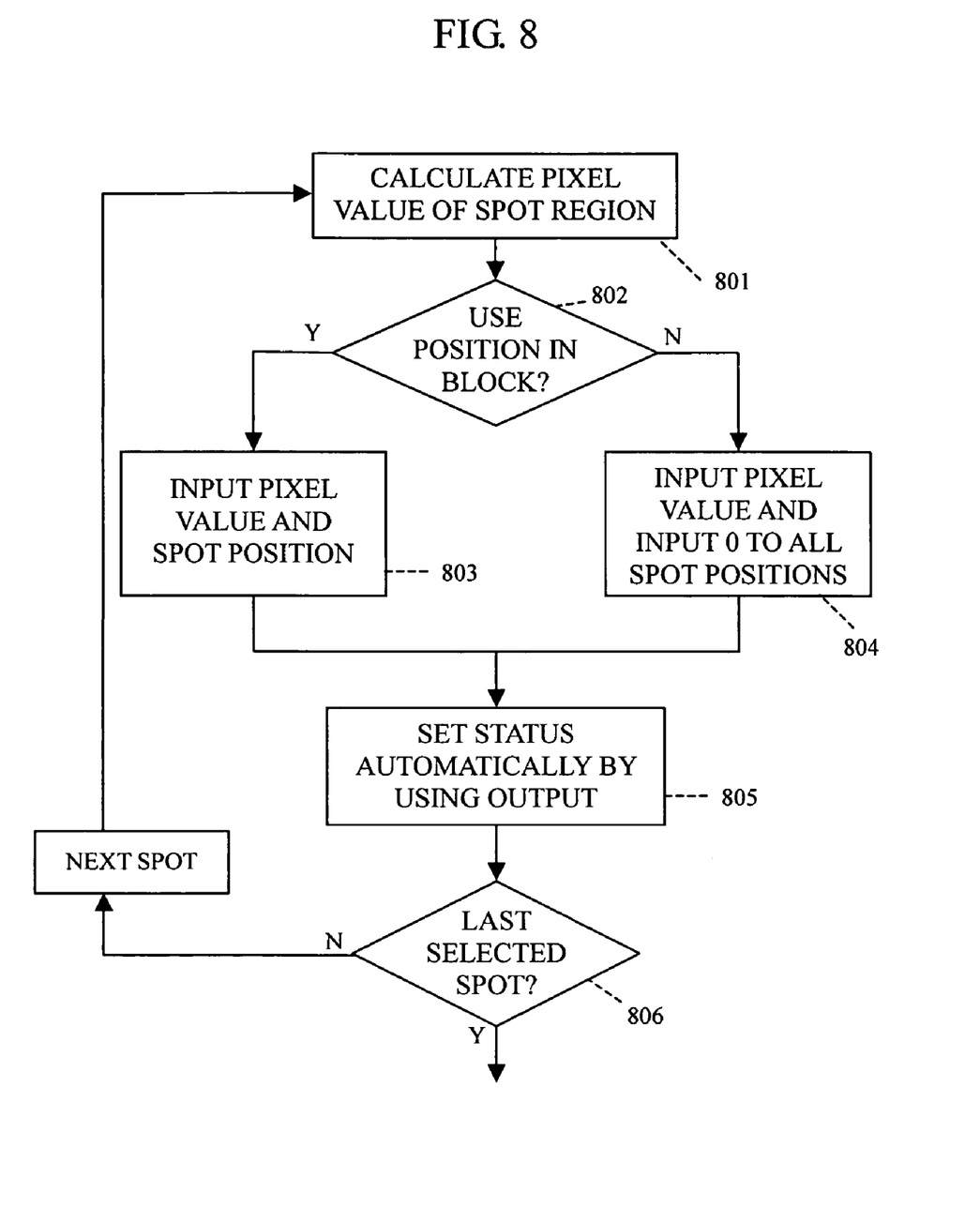
FIG. 8 is a flowchart showing a part for automatic decision.

When it is decided in step 605 that learning is not selected, that is when automatic decision is selected, automatic decision is performed in step 610. The detail is shown in FIG. 8. In step 611, the user decides whether the system should be ended or not. When the system is not ended, for example, when learning is started over, the processing returns to step 604 and a spot is selected again.

Figure 7:
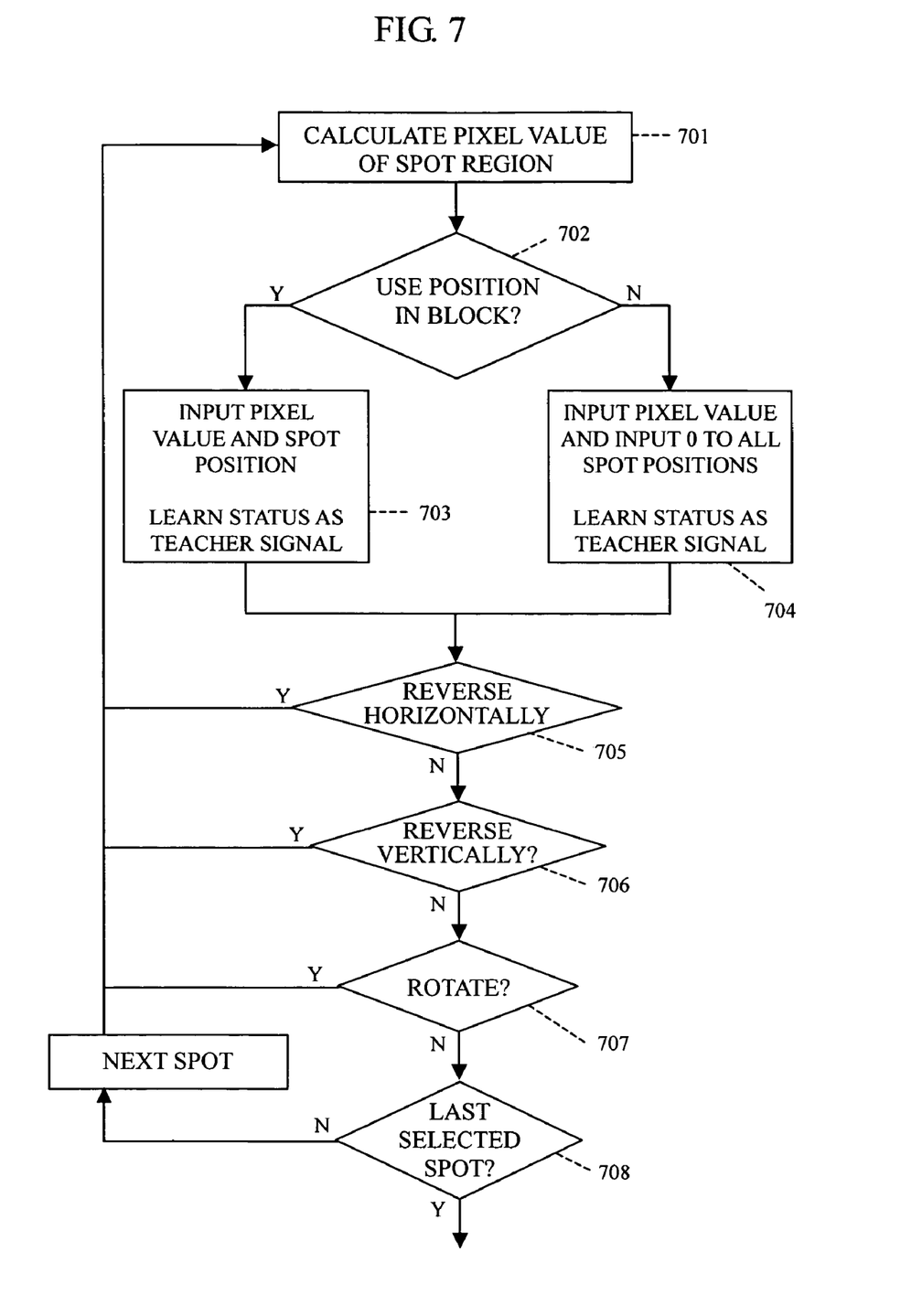
FIG. 7 is a flowchart showing a part for learning.

FIG. 7 is a flowchart showing the learning of step 607. In step 701, a pixel value in the spot region of one spot is calculated. Step 702 is a branching step depending upon whether or not learning is performed using a spot position in a block. In step 703, a spot position in a block is used. A pixel value and a spot position are inputted to the feed-forward neural network and learning is performed with a status serving as a teacher signal. In step 704, a spot position in a block is not used. A pixel value is inputted as it is to the feed-forward neural network but 0 is inputted to all units for inputting spot positions, and learning is performed with a status serving as a teacher signal.

In step 705, an image of a spot region is horizontally reversed. When a horizontally reversed image has not been inputted to the feed-forward neural network, the processing returns to step 701 to calculate a pixel value and learning is performed. In step 706, an image of a spot region is vertically reversed. When a vertically reversed image has not been inputted to the feed-forward neural network, the processing returns to step 701 to calculate a pixel value and learning is performed. In step 707, an image of a spot region is rotated. When a rotated image has not been inputted to the feed-forward neural network, the processing returns to step 701 to calculate a pixel value and learning is performed. In step 708, it is decided whether selected spots are all used for learning. When there is a spot not being used for learning, the processing returns to step 701 to calculate a pixel value of the spot.

FIG. 8 is a flowchart showing the automatic decision of step 710. In step 801, a pixel value in the spot region of one spot is calculated. Step 802 is a branching step depending upon whether or not automatic decision is performed using a spot position in a block. Step 803 is a case where a spot position in the block is used, a pixel value and a spot position are inputted to the feed-forward neural network and output results are obtained. When learning is performed in a setting not using a spot position in a block, combined loads remain initial values of sufficiently small random numbers and thus any spot position in a block does not affect the results. In step 804, a spot position in a block is not used. A pixel value is inputted as it is to the feed-forward neural network but 0 is inputted to all units for inputting spot positions and output results are obtained. When learning is performed in a setting using a spot position in a block, 0 is inputted to all units for inputting spot positions and thus any spot position in a block does not affect the results. In step 805, a status of a spot is decided using the output results of the feed-forward neural network. In the case of a system not permitting the setting of two or more statuses for one spot, a status of the output unit closest to 1 is adopted. In step 806, it is decided whether selected spots are all used for automatic decision. When there is a spot not being used for automatic decision, the processing returns to step 801 to calculate a pixel value of the spot.

According to the present invention described above, in the process at some midpoint of an expression analysis from a DNA microarray image, for the setting of a status on a spot which is unsuitable for an expression analysis due to the intrusion of dirt and a contamination and a spot which is somewhat significant for other reasons, decision is automatically performed by causing the feed-forward neural network to learn the decision of the user and thus the working time of the user is shortened, and the accuracy of an expression analysis is improved by preventing a mistake and an oversight.

In this case, by setting a status of one spot, a vertically and horizontally reversed spot image and a rotated spot image are automatically formed and learned, thereby enhancing the effect of automation.

Further, in consideration of a characteristic in that spots having similar spot coordinates in a block are prone to have similar statuses in a spotter of a DNA microarray, a spot position in a block can be optionally inputted to the feed-forward neural network. Regarding this function, whether a spot position in a block should be used or not is switched in the same network, thereby eliminating the necessity for relearning.

By adding the function of storing and reading learning results, feed-forward neural networks to be used can be switched according to the kind of DNA microarray.

What is claimed is:

1. A DNA microarray image analysis system which reads a DNA microarray image after hybridization and utilizes a feed forward neural network to analyze statuses of each spot of the DNA microarray image, wherein the DNA microarray is a Stanford type microarray having a plurality of blocked spot regions, the feed forward neural network includes a plurality of pixel value input units by the number of the plurality of pixels in one spot region and output units by the number of a plurality of statuses, and the output units correspond to the plurality of statuses which can be set in the one spot, region, the system comprising:

a learning section for using as a teacher signal a status set in a spot region by a user, for inputting a plurality of pixel values in the spot region to the plural pixel value input units and for controlling the feed forward neural network to learn criteria to determine the statuses set in the spot region; and an automatic decision section for providing the plurality of pixel input units of the feed forward neural network after learning operation with a plurality of pixel values in a spot region designated by the user where statuses have not been set, to determine the statuses of the designated spot region.

2. The DNA microarray image analysis system according to claim 1, wherein the learning section reverses an image of the spot region horizontally, vertically, or vertically and horizontally, and wherein if the reversed image is not included in images input in the feed forward neural network, the learning section inputs a plurality of pixel values to plurality of pixel value input units and controls the feed forward neural network to learn the criteria to determine the status set in the spot region by the user using the teacher signal.

3. The DNA micro array image analysis system according to claim 1, wherein the learning section rotates an image of the spot region by 90°, 180°, or 270°, and wherein if the rotated image is not included in images input in the feed forward neural network, the learning section inputs a plurality of pixel values to plurality of pixel value input units and controls the feed forward neural network to learn the criteria to determine the status set in the spot region by user using the teacher signal.

4. The DNA microarray image analysis system according to claim 1, wherein the feed forward neural network further includes a spot position input unit for inputting a position in a block of the spot region, and wherein the learning section inputs the position in the block of the spot region where the status has been set by the user to control the feed forward neural network to learn the criteria to determine the status set in the spot region by the user using the teacher signal.

5. The DNA microarray image analysis system according to claim 1, wherein a plurality of statuses are not permitted to be set in one spot region in the system, the neural network utilizes a sigmoid function to calculate expected values of the plurality of output units, and the automatic decision section provides the plurality of pixel input units of the feed forward neural network after the learning operation with a plurality of pixel values included in the image of the spot region designated by the user where the status has not been set and the automatic decision section outputs the plurality of expected values of the status which can be set in the spot region to each of the plurality of output units to set a status corresponding to an output unit for storing an expected value closest to 1 to the status of the spot region where the status value has not been set.

6. The DNA microarray image analysis system according to claim 1, wherein the status automatic decision section provides the spot position input unit with the position in the block of the spot region designated by the user where the status has not been set to determine the status of the spot region where the status has not been set.

7. A computer-readable recording medium for storing a DNA microarray image analysis program executed by a computer, the program reading a DNA microarray image after hybridization and utilizes a feed forward neural network to analyze statuses of each set of the DNA microarray image, wherein the feed forward neural network includes a plurality of pixel value input units by the number of the plurality of pixels in one spot region and output units by the number of a plurality of statuses, and wherein the output units correspond to the plurality of statuses which can be set in the one spot region, the program performing:

a learning step of using as a teacher signal a status set in a spot region by a user, for inputting a plurality of pixel values in the spot region to the plural pixel value input units and for controlling the feed forward neural network to learn criteria to determine the statuses set in the spot region;

an automatic decision step of providing the plurality of pixel input units of the feed forward neural network after learning operation with a plurality of pixel values in a spot region designated by the user where statuses have not been set, to determine the statuses of the designated spot region.

* * * * *